United States Patent [19]

Szarek et al.

[11] 4,207,413

[45] Jun. 10, 1980

[54] L-SUCROSE AND PROCESS FOR PRODUCING SAME

[75] Inventors: Walter A. Szarek, Kingston, Canada; John K. N. Jones, deceased, late of Kingston, Canada, by Marjorie I. Jones, executrix

[73] Assignee: Queen's University at Kingston, Kingston, Canada

[21] Appl. No.: 895,922

[22] Filed: Apr. 13, 1978

[30] Foreign Application Priority Data

Apr. 22, 1977 [CA] Canada .................................. 276796

[51] Int. Cl.$^2$ .............................................. C07H 3/04
[52] U.S. Cl. ........................................... 536/1; 536/4; 536/122
[58] Field of Search ................................ 536/1, 4, 120

[56] References Cited

PUBLICATIONS

Lemieux, R., et al., J. Am. Chem. Soc. 78, 4117 (1956).
Hassid and Ballou, "The Carbohydrates", Pigman, Ed., Academic Press Inc., New York, 1957, p. 483.
Berry et al., "Chem. Abst.", vol. 82, 1975, 98280g.
King et al., "Chem. Abst.", vol. 83, 1975, 179439p.

*Primary Examiner*—Johnnie R. Brown
*Assistant Examiner*—Blondel Hazel
*Attorney, Agent, or Firm*—Richard J. Hicks; Stanley E. Johnson

[57] ABSTRACT

L-sucrose or β-L-fructofuranosyl α-L-glucopyranoside—(I), the enantiomer of naturally occuring D-sucrose, which does not appear in nature has been synthesized and has been found to be sweet. It is unlikely that L-sucrose is metabolized in the manner of D-sucrose. In a preferred process for producing L-sucrose the key step is the condensation of 2,3,4,6-tetra-O-benzyl-α-L-glucopyranosyl chloride—(II) with 1,3,4,6-tetra-O-benzyl-L-fructofuranose—(III). Compound II is obtained from L-glucose by way of 2,3,4,6-tetra-O-benzyl-α-L-glucopyranose; and L-glucose is prepared from L-arabinose by nitromethane synthesis. Compound III is obtained by oxidation, with Jones reagent, of 1,3,4,6-tetra-O-benzyl-L-mannitol which, in turn, is prepared from L-mannose. The condensation product of II and III is catalytically debenzylated to produce L-sucrose.

1 Claim, No Drawings

L-SUCROSE AND PROCESS FOR PRODUCING SAME

This invention relates to sweetening agents and a process for producing them. More particularly this invention relates to the production of L-sucrose (β-L-fructofuranosyl α-L-glucopyranoside).

Sucrose is, of course, the major nutritive sweetener in the human diet and is almost ubiquitous in the plant kingdom. In plants it functions as an energy source for metabolic processes and as a carbon source for the biosynthesis of cellular components. Sucrose for human consumption has been produced for thousands of years from a variety of natural sources, the principal ones of which are sugar cane and sugar beet and others such as sugar maple and sorghum. Sucrose, $C_{12}H_{22}O_{11}$, is a disaccharide and can therefore theoretically occur in any one of four stereoisometric forms. Sucrose from all known natural sources occurs as the D-enantiomer and there is no evidence of the L-enantiomer in nature. Many attempts to synthesize sucrose, the molecule of which is an α-glycoside a structural unit whose synthesis has been one of the classical problems of carbohydrate chemistry, have been made and the first success in this area was reported by Lemieux and Huber (J. Am. Chem. Soc. 75, 4118 [1953]) for the production of D-sucrose. Heretofore the mirror image (enantiomer) of the D-sucrose molecule has been unknown, and the synthesis thereof is described for the first time in this specification. Although the enantiomers of all chiral compounds are chemically identical, they differ in their optical properties and, in most cases, in their biological properties including organoleptic properties. For example L-fructose, a sugar which has not yet been detected in nature, was synthesized by Fischer in 1890 by treating α-acrose with phenylhydrazine. The resulting D L-glucose phenylosazone was isolated and hydrolysed to the glycosulose which was then reduced to D L-fructose. The D-fructose was then fermented with yeast, to yield a solution of L-fructose. It will be appreciated from the above that although the D-fructose is subject to fermentation by yeast, the L-fructose is not affected by yeast. Many similar examples exist with respect to other sugars, yeasts and other enzymes. It is known that enzymes are specific to specific enantiomers and that enzymes do not normally adapt to break down alternative or different enantiomers unless there is some specific latent triggering mechanism. As L-sucrose is not known in nature there is no reason to believe that an enzyme for L-sucrose should exist in nature nor that any existing enzyme could adapt to L-sucrose. It is believed, therefore, that L-sucrose, which is in itself sweet, is not metabolized in the human body and is therefore not a food but is, rather a food additive.

It is an object of the present invention to provide a novel sweetener comprising L-sucrose, a sugar which has not been detected in nature.

It is another object of the present invention to provide a process for the preparation of L-sucrose.

Thus by one aspect of this invention there is provided α-L-fructofuranosyl α-L-glycopyranoside.

By another aspect of this invention there is provided a process for producing β-L-fructofuranosyl α-L-glucopyranoside which comprises condensing a compound having the formula:

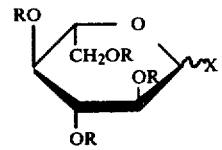

with a compound having the formula:

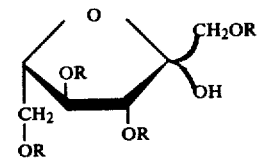

so as to produce a compound having the formula:

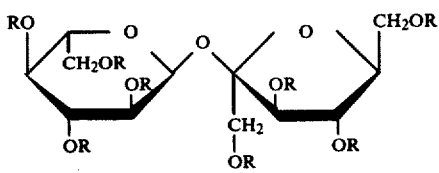

where X is selected from the group comprising Cl, Br and I and R is aralkyl, lower alkyl or lower alkenyl, and converting said product so as to produce a compound having the formula:

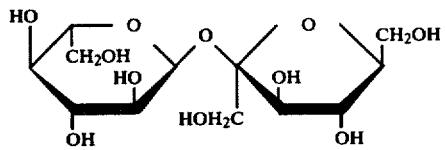

L-sucrose is a disaccharide having the formula:

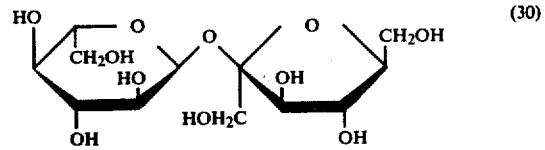

(30)

that is L-glucopyranose and L-fructofuranose joined through their anomeric centers by an α linkage in the former and a β linkage in the latter. As neither of these constituent molecules is readily available, a prerequisite to the synthesis of L-sucrose is the synthesis of appropriate derivatives L-glucopyranose and L-fructofuranose.

This involves the ascent of the series from readily available L-arabinose (33) to produce an epimeric mixture of 6-carbon carbohydrates which can be separated and individually treated to give the desired L-glucopyranose (31) and L-mannopyranose (36). This may be effected by a nitro methane condensation of L-arabinose to produce an epimeric mixture of 1-deoxy-1-nitro hexitols (34 and 35) which can be separated and individually treated with strong acid. Conversion of L-mannopyranose to the desired L-fructose (32) can then be carried out by initial formation of the osazone (37) followed by exchange of the nitrogenous functions with oxygen to give L-arabino-hexosulose (38) which has been shown to be selectively reducible to L-fructose (32).

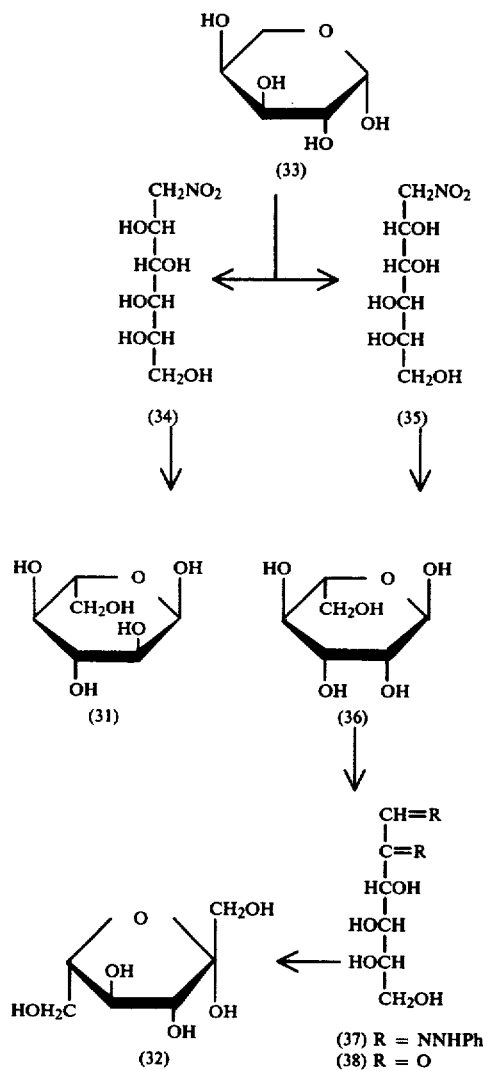

The subsequent condensation of L-glucopyranose with L-fructofuranose to give L-sucrose then requires that one of the molecules be converted into a suitably blocked glycosyl halide, whereas the other be protected in such a way so as to preclude reaction at all sites save the anomeric position. A number of blocking groups are available for this type of reaction and for the synthesis of L-sucrose the benzyloxy function, as used by Ness and Fletcher (carbohyd. Res. 17, 465 [1971]) in their synthesis of D-sucrose, is particularly suitable.

The route to L-sucrose then involves the formation of 1,3,4,6-tetra-O-benzyl-L-mannitol (51) from L-mannose (36) by way of L-mannitol (46). The end-to-end symmetry of mannitol makes the hydroxyl groups in (51) equivalent. Oxidation of one of these hydroxyl groups would be followed by rapid formation of a hemiacetal effectively blocking the second hydroxyl group from further oxidation and yielding the desired 1,3,4,6-tetra-O-benzyl-L-fructofuranose (45).

The condensation of L-arabinose (33) with nitromethane in alkaline methanol may be carried out according to the method of Sowden (J. Amer. Chem. Soc. 69, 1963[1974]) to give a mixture of the nitro alcohols (34) and (35). Recrystallization of the separated 1-deoxy-1-nitro-L-glucitol (34) affords a pure product which can be used in the synthesis of L-glucose by treatment of the sodium salt with concentrated sulfuric acid (Nef degradation).

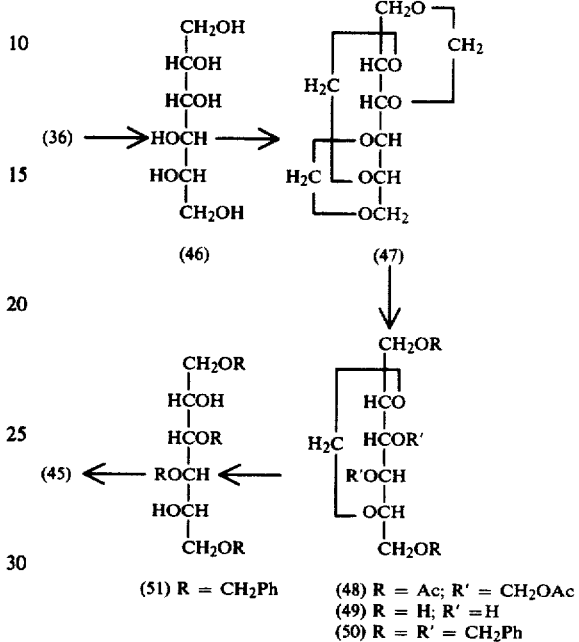

The formation of methyl L-glucopyranoside (39) may be carried out by condensing anhydrous α-L-glucopyranose with methanol preferably in the presence of a catalytic cation-exchange resin according to the method of Bollenback (Methods Carbohyd. Chem. 2, 326[1963]). Blocking of methyl L-glucopyranoside, such as by benzylation and subsequent hydrolysis to 2,3,4,6-tetra-O-benzyl-α-L-glucopyranose (41), may be carried out using various methods. Firstly methyl 2,3,4,6-tetra-O-benzyl-L-glucopyranoside (40) may be formed from the syrupy methyl L-glucopyranoside using the method of Tate and Bishop (Can. J. Chem. 41, 1801[1963]) in which the reaction is carried out in 1,4-dioxane with powdered potassium hydroxide and benzyl chloride. The resultant reaction mixture may contain substantial amounts of benzyl alcohol and dibenzyl ether (both of which are difficult to remove) along with an anomeric mixture of methyl 2,3,4,6-tetra-O-benzyl-L-glucopyranoside.

An alternative procedure which is very effective is modelled on the work of Iwashige and Saeki (Chem. Pharm. Bull. Jap. 15, 1803 [1967]) involves alkylation with dimethyl sulfoxide at low temperature and with only a small excess of both basic reagent and benzyl chloride.

The hydrolysis of methyl 2,3,4,6-tetra-O-benzyl-L-glucopyranoside may be carried out in glacial acetic acid and dilute sulphuric acid as formulated by Tate and Bishop (supra) to produce 2,3,4,6-tetra-O-benzyl-L-glucopyranose which can be reacted with thionyl chloride to form 2,3,4,6-tetra-O-benzyl-L-glucopyranosyl chloride. Halogenation of 2,3,4,6-tetra-O-benzyl-L-glucopyranose with zinc chloride-thionyl chloride results in a homogeneous 2,3,4,6-tetra-O-benzyl α-L- glucopyranosyl chloride product. In an alternative procedure, methyl 2,3,4,6-tetra-O-benzyl-α-L-glucopyranoside may be refluxed with thionyl chloride (48 hours at 5° C.) to produce 2,3,4,6-tetra-O-benzyl-L-glucopyranosyl chloride.

The formation of 1,3,4,6-tetra-O-benzyl-L-fructofuranose

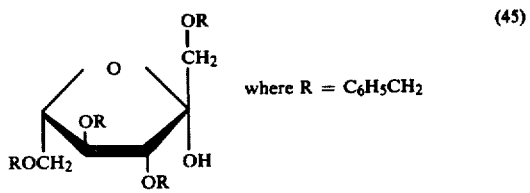

(45) where R = C$_6$H$_5$CH$_2$ from L-mannose involves the reduction of L-mannose (36) to L-mannitol (46) from which the cyclic acetal 2,5-O-methylene-L-mannitol (49) is readily available. Alkylation with benzyl chloride followed by cleavage of the acetal bridge leads to 1,3,4,6-tetra-O-benzyl-L-mannitol (51). The end-to-end symmetry of mannitol makes the hydroxyl groups in (51) equivalent.

The reaction of L-mannose to L-mannitol may be carried out in various ways such as using sodium borohydride in water. As L-mannitol is somewhat difficult to crystallize it is advisable to treat the L-mannitol solution with concentrated HCl and formaldehyde to produce highly crystalline 1,3:2,5:4,6-tri-O-methylene-L-mannitol (47).

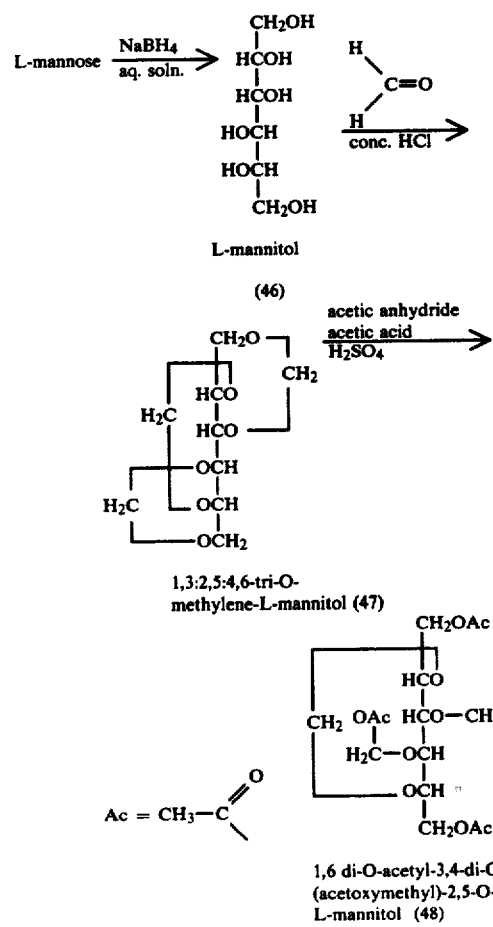

1,3:2,5:4,6-tri-O-methylene-L-mannitol (47)

1,6 di-O-acetyl-3,4-di-O-(acetoxymethyl)-2,5-O-methylene-L-mannitol (48)

Ac = CH$_3$—C(=O)

The subsequent ring fission of (47) to give 1,6-di-O-acetyl-3,4-di-O-(acetoxymethyl)-2,5-O-methylene-L-mannitol (48) may be effected with an acetolysis mixture of acetic anhydride, acetic acid and sulfuric acid. Although less preferred, a mixture of trifluoroacetic acid and acetic acid may also be employed. Compound 48 can be de-O-acetylated in various ways such as using 0.2 N methanolic sodium methoxide to give crystalline 2,5-O-methylene-L-mannitol (49) which can be protected such as by aralkylation with benzyl chloride to yield 1,3,4,6-tetra-O-benzyl 2,5-O-methylene-L-mannitol (50).

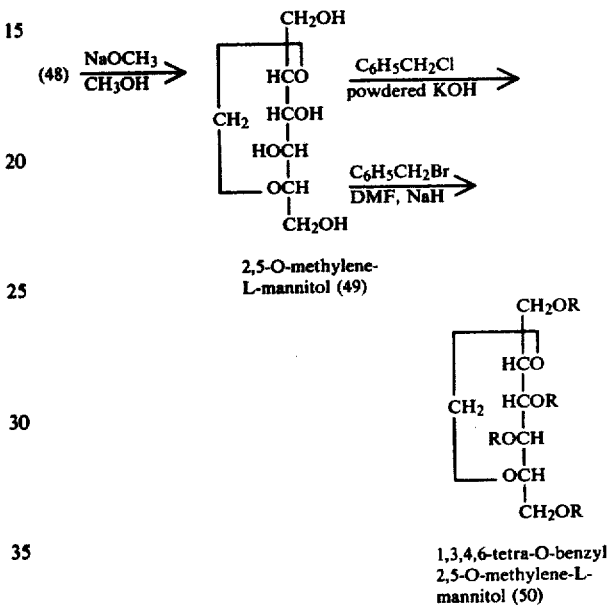

2,5-O-methylene-L-mannitol (49)

1,3,4,6-tetra-O-benzyl 2,5-O-methylene-L-mannitol (50)

The hydrolysis of 50 to give 1,3,4,6-tetra-O-benzyl-L-mannitol (51) may be effected by refluxing with 0.6 MHCl and phloroglucinol. 90% aqueous trifluoroacetic acid may also be used for this purpose.

The next step, to oxidize 51 to 1,3,4,6-tetra-O-benzyl-L-fructofuranose (45), may be effected in any known manner but the use of Jones reagent (a mixture of chromium trioxide, sulfuric acid and water) is to be preferred.

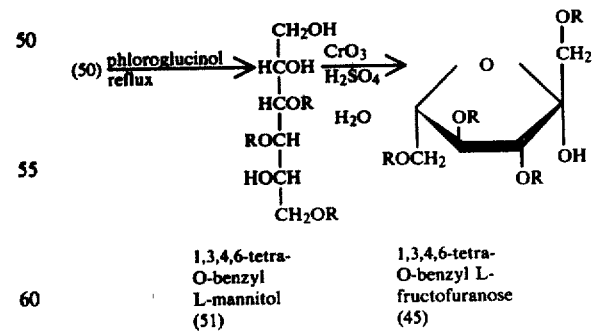

1,3,4,6-tetra-O-benzyl L-mannitol (51)

1,3,4,6-tetra-O-benzyl L-fructofuranose (45)

The condensation of 1,3,4,6-tetra-O-benzyl-L-fructofuranose (45) with 2,3,4,6-tetra-O-benzyl-α-L-glucopyranosyl chloride (42) may be effected using silver perchlorate, silver carbonate and molecular sieves, in dry benzene, under nitrogen and in the dark, to produce two components one chromatographically identical to previously known octa-O-benzyl-D-sucrose and the other having a chromatographic mobility just slightly less than the first. Fractionation on silica gel produced a compound 1,3,4,6-tetra-O-benzyl-β-L-fructofuranosyl 2,3,4,6-tetra-O-benzyl-α-L-glucopyranoside and catalytic debenzylation over 5% palladium on charcoal in methanol affords L-sucrose whose physical constants are consistent with those of the D-enantiomer.

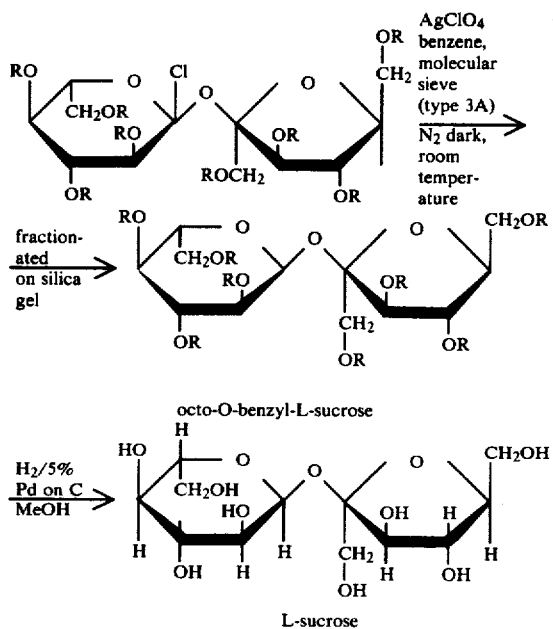

EXAMPLE 1

1-Deoxy-1-nitro-L-glucitol (34) and 1-deoxy-1-nitro-L-mannitol (35)

A suspension of commercial α-L-arabinose (100 g.) in absolute methanol (200 ml.) and dry nitromethane (360 ml.), in a 3-necked, 2-liter flask fitted with an efficient mechanical stirrer and a calcium chloride drying tube, was treated with a 1.3 N methanolic sodium methoxide solution (700 ml.). After 20 hr. of vigorous stirring, the precipitated sodium aci-nitro alcohols were collected by filtration and washed with a small volume of cold methanol followed by cold petroleum ether (60°–80°). The moist, highly hygroscopic salts were immediately dissolved in 800 ml. of iced water and the solution de-ionized either by passage over a column containing 800 ml. of Dowex ® 50W-X8 (H+) resin or by three successive treatments with 300 ml. of fresh resin. The effluent and washings (total volume 2.5–3.0 liters for the column treatment and 1.5–2.0 liters for the batch treatment) were then evaporated at reduced pressure to a semi-crystalline mass which was further concentrated with several portions of absolute ethanol to remove residual water. The resulting crystalline mass was filtered with the aid of cold ethanol and the filtrate reprocessed to provide two additional crops of crystals. The crude product (70 g.) was separated by fractional crystallization from ethanol into the less soluble 1-deoxy-1-nitro-L-mannitol (30 g.) and the more soluble 1-deoxy-1-nitro-L-glucitol (25 g.). Two additional recrystallizations of samples of the nitro alcohols provided 1-deoxy-1-nitro-L-glucitol, m.p. 106°–107°, $[\alpha]_D + 7.44°$ (c 3.2, water), compared to m.p. 107°–108°, $[\alpha]_D + 9.5°$ (c 6.7, water); and 1-deoxy-1-nitro-L-mannitol, m.p. 133°–134°, $[\alpha]_D + 6.67°$ (c 5.4, water), compared to m.p. 133°–134°, $[\alpha]_D + 7.0°$ (c 6.2, water).

EXAMPLE 2

α-L-Glucopyranose (31)

1-Deoxy-1-nitro-L-glucitol (5.0 g.) was dissolved in 2 N sodium hydroxide (15 ml.) and the solution was immediately added dropwise to a stirred, cooled (ice-bath) solution of sulfuric acid (7.5 ml.) in water (9.0 ml.). The solution was then diluted with water (175 ml.) and neutralized to Congo Red with warm barium hydroxide solution. The precipitated barium sulfate was removed by centrifugation and the remaining sulfate was precipitated with a slight excess of barium acetate. The solution was then filtered through a pad of Celite ® and the filtrate de-ionized by passage through a column containing 50 ml. of Dowex ® 50W-X8 (H+) resin. The effluent and washings were evaporated under reduced pressure to a syrup which was diluted with a few drops of ethanol, warmed to 50°, seeded (seed crystals obtained from previous experiments) and allowed to crystallize. The resulting crystals were filtered with the aid of cold ethanol to give, after recrystallization, α-L-glucopyranose (2.4 g.), m.p. 146°–147°, $[\alpha]_D - 100° \rightarrow -53.3°$ (24 hr.; c 2.15, water), compared to m.p. 146°–147°, $[\alpha]_D - 53°$ (at equilibrium; c 2.6, water). The filtrate containing L-glucose (t.l.c., n-propanol/ethyl acetate/water v/v 3:1:1) was retained for use in subsequent preparations of L-glucose.

EXAMPLE 3

Methyl α-L-glucopyranoside (39)

A mixture of α-L-glucopyranose (5.4 g.), methanol (30 ml.) and cation-exchange resin [(2 g., Dowex ® 50W-X8 (H+), 50–100 mesh, previously prepared by treatment with methanol] was stirred magnetically at reflux temperature for 24 hours in a 50-ml. round-bottomed flask. The solution, which gave a negative test, was then cooled and filtered. The resin was washed several times with methanol and the filtrate and washings were evaporated at reduced pressure to a syrup (5.63 g., 96%) containing no L-glucose (paper chromatography, n-butanol/ethanol water v/v 40:11:19). A sample (1.0 g.) was dissolved in boiling methanol (2 ml.) and the mixture was allowed to slowly cool to room temperature to give crystalline methyl L-glucopyranoside. The crystals were suspended in enough ethanol to make a 10% (w/v) mixture, and this mixture was boiled to effect dissolution. On cooling of the mixture pure methyl α-L-glucopyranoside was obtained, m.p. 166.5°–168°, $[\alpha]_D - 156°$ (c 2.5, water). These values compare favourably with those for methyl α-D-glucopyranoside, m.p. 167°–169°, $[\alpha]_D + 157°$ (c 2, water).

EXAMPLE 4

Methyl 2,3,4,6-Tetra-O-benzyl-L-glucopyranoside (40)

(a) Using potassium hydroxide and benzyl chloride

Powdered potassium hydroxide (25 g.) was added to a magnetically stirred solution of syrupy methyl L-glucopyranoside (4.8 g.) in dry 1,4-dioxane (30 ml.). This stirred solution was gently heated on an oil bath (reflux), and freshly distilled benzyl chloride (32 ml.) was added dropwise over a 1 hour period. Heating and stirring were continued for an additional 4 hour period, at which time the dioxane was distilled and the resultant mixture cooled, diluted with water (200 ml.) and extracted with chloroform (3×75 ml.). The chloroform extracts were then washed with dilute hydrochloric acid and then with water. The chloroform layer was dried over sodium sulfate and then concentrated at reduced pressure to a syrup (17 g.) which was seen to contain three components (t.l.c., benzene/ethyl acetate 10:1 v/v) having $R_f$ values of approximately 0.4, 0.48, and 0.73. T.L.C. comparison (benzene/ethyl acetate 10:1 v/v) of this mixture with the previously prepared methyl 2,3,4,6-tetra-O-benzyl-D-glucopyranosides and also with benzyl ether showed that the component with the greatest mobility was benzyl ether whereas the one having the least mobility was likely the α-anomer and the middle component the β-anomer. A small portion of this reaction mixture was purified by column chromatography on silica gel by eluting first with benzene to remove benzyl ether and then with a 10:1 mixture of benzene-ethyl acetate to give methyl 2,3,4,6-tetra-O-benzyl-α-L-glucopyranoside as a syrup having $[\alpha]_D -25.4°$ (c 3.8, chloroform) as compared with $[\alpha]_D +23.8°$ (c 3.42, chloroform), or $[\alpha]_D +18.7°$ (c 1.5, chloroform) for methyl 2,3,4,6-tetra-O-benzyl-α-D-glucopyranoside, and crystalline methyl 2,3,4,6-tetra-O-benzyl-β-L-glucopyranoside having m.p. 69.5°–70°, $[\alpha]_D -12.1°$ (c 4.2, dioxane) as compared to m.p. 68°–69°, $[\alpha]_D +11°$ (c 5.3, dioxane) for methyl 2,3,4,6-tetra-O-benzyl-β-D-glucopyranoside.

(b) Using sodium hydride/dimethyl sulfoxide and benzyl chloride

Methyl L-glucopyranoside (2.0 g.) in dimethyl sulfoxide (10 ml.) was added dropwise to a solution of sodium hydride (1.0 g.) in dimethyl sulfoxide (10 ml.), the solution being stirred under nitrogen. After the addition of the glycoside, the solution was stirred at room temperature for an additional 40 min., at which time benzyl chloride (8.0 g.) was added dropwise, and the solution stirred for a further 1.5 hr. The reaction mixture was poured into iced water (50 ml.) and the solution extracted with ether (3×50 ml.). The ether layer was dried (magnesium sulfate) and concentrated at reduced pressure to a syrup which contained a mixture of the tetra-O-benzyl glycosides along with some benzyl chloride (t.l.c., benzene/ethyl acetate 10:1 v/v). The syrup was chromatographed on silica gel (150 g.), eluting initially with benzene to remove benzyl chloride, followed by a 10:1 mixture of benzene-ethyl acetate to obtain an anomeric mixture of methyl 2,3,4,6-tetra-O-benzyl-L-glucopyranoside (5.1 g., 89%).

EXAMPLE 5

2,3,4,6-Tetra-O-benzyl-α-L-glucopyranose (41)

The crude mixture of methyl tetra-O-benzyl-L-glucopryanoside (16 g.) was dissolved in glacial acetic acid (275 ml.) and the solution was heated on a steam bath. To this heated solution was then added 2 N sulfuric acid (75 ml.) over a period of 2 hr., in portions, so as to prevent the formation of a syrup. Subsequently, an additional amount of 2 N sulfuric acid (60 ml.) was carefully added and the solution was heated an additional 20 hr. The reaction mixture was then cooled, poured into one liter of water and the resultant mixture left overnight at 5°. The precipitate which formed was removed by filtration and recrystallized from methanol to give pure 2,3,4,6-tetra-O-benzyl-α-L-glucopyranose, m.p. 145.5°–146.5°, $[\alpha]_D -21.1°$ (c 2.8, chloroform), compared to m.p. 151°–152° (Corr.), $[\alpha]_D +21.7°$ (c 2.19, chloroform) observed for the D-isomer. P.M.R. data: τ2.6–2.8 (20 aromatic protons), τ4.7 (1-proton multiplet, anomeric proton), τ5.1–6.6 (15 protons, ring protons and benzylic —CH$_2$—), τ6.8 (1-proton doublet, anomeric-OH, exchangeable with D$_2$O). When D$_2$O was added to the p.m.r. sample the 1-proton signal at τ6.8 collapsed and the 1-proton signal at τ4.7 became a doublet with a coupling constant of $J_{1,2} \simeq 4$ Hz indicating that the α-anomer had in fact been obtained.

EXAMPLE 6

2,3,4,6-Tetra-O-benzyl-L-glucopyranosyl chloride (42)

Method A—Pure 2,3,4,6-tetra-O-benzyl-α-L-glucopyranose (500 mg.) was dissolved in purified thionyl chloride in a 25 ml. round-bottomed flask equipped with a condenser and a drying tube, and the solution was stirred (magnetically) at 70° (oil bath). The progress of the reaction was monitored by t.l.c. (benzene/diethyl ether 6:1 v/v) and at the end of 4 hours a major component was visible having $R_f \simeq 0.8$ and two minor components having $R_f \simeq 0.5$. A trace of starting material was also noted, however this was rationalized as being a result of the hydrolysis of the product on the t.l.c. plate (an assumption which had been previously confirmed with reactions in the D-series). The solution was then cooled and concentrated at reduced pressure to a reddish syrup. The excess of thionyl chloride was removed by distillation with dry toluene (4×10 ml.) and then dry benzene (2×10 ml.). The dark syrup was then dissolved in dry benzene (10 ml.) and used immediately in the disaccharide synthesis or in subsequent reactions.

Method B—2,3,4,6-Tetra-O-benzyl-α-L-glucopyranose (400 mg.) was dissolved in dry benzene (25 ml.) in a round-bottomed flask equipped with a calcium chloride drying tube and an inlet for nitrogen. To the magnetically stirred solution was added zinc chloride (1.1 g.) followed by thionyl chloride (0.55 ml.) care being taken to exclude atmospheric moisture. The reaction, which was monitored by t.l.c. (Solvent D), was complete after approximately 45 minutes. The solution was then filtered through a 3 cm. thickness of silica gel on a sintered glass funnel and the residue washed with dry benzene. The filtrate was then concentrated under reduced pressure to a colourless syrup which was co-evaporated with benzene (40 ml.) at 30° bath to remove traces of thionyl chloride. The colourless syrup (0.31 g.) was homogeneous on t.l.c. (benzene/diethyl ether 10:1 v/v) and had $[\alpha]_D -62.5°$ (c 2.1, chloroform) and the following p.m.r. data: τ2.7 (20 aromatic protons), τ3.9 (1 proton, H-1, doublet with $J_{1,2} \simeq 3$ Hz.), τ5.1–6.6 (15 protons, ring protons and benzylic —CH$_2$—). The corresponding D-isomer has $[\alpha]_D +109°$ (c 1, benzene), +62° (c 1, chloroform) as found by Grob et al [Carbohyd. Res. 10 595 (1964)] and $[\alpha]_D +95°$ (c 4.0, benzene), +66° (c 6.3, benzene) as found by Austin et al [J. Chem. Soc., 2128 (1964)].

EXAMPLE 7

L-Mannose (36)

1-Deoxy-1-nitro-L-mannitol (20 g.) was dissolved in 2 N sodium hydroxide (60 ml.), and the solution was immediately added dropwise to a stirred solution of sulfuric acid (30 ml.) in water (36 ml.) at room temperature. Some cooling (ice bath) was used to keep the reaction mixture at 22°±5°. The solution was then diluted to 400 ml. with water, just neutralized with solid sodium hydrogen carbonate, and a solution of phenylhydrazine (12 ml.) in glacial acetic acid (28 ml.) added. The mixture was stirred overnight at 5° and then filtered, and the L-mannose phenylhydrazone was washed with cold water, ethanol, and ether. Recrystallization from ethanol gave pure L-mannose phenylhydrazone, m.p. 198°–199°, $[\alpha]_D-33.5°$ (c 2.5, pyridine) compared with m.p. 199°–200°, $[\alpha]_D+34°$ for the D-isomer, p. 240).

The hydrazone (20 g.) was then refluxed for 3 hours with a solution containing water (200 ml.), ethanol (40 ml.), benzaldehyde (25 ml.) and benzoic acid (2.5 g.). The solution was cooled and then decanted from benzaldehyde phenylhydrazone, extracted three times with chloroform, decolorized with carbon and concentrated at reduced pressure. The resulting syrup was further evaporated with several portions of absolute ethanol to remove residual water and the resulting syrup (10 g.) was left to crystallize. The crystals were filtered with ethanol to give α-L-mannopyranose, m.p. 125°–126°, $[\alpha]_D-26.9° \rightarrow -14.4°$ (24 hr., c 2.0, water) compared to m.p. 128°–132°, $[\alpha]_D-14.5°$ (equilibrium, c 3.4, water).

L-Mannose was also obtained directly from the nitromethane condensation by carrying out the Nef degradation on the precipitated sodium aci-nitro alcohols followed by the phenylhydrazone formation in which only the water-insoluble L-mannose phenylhydrazone precipitated from the aqueous solution. Cleavage of the nitrogenous derivative was then carried out as described above.

EXAMPLE 8

L-Mannitol (46)

A solution of sodium borohydride (2.0 g.) in water (50 ml.) was added dropwise to a stirred solution of L-mannose (15 g.) in water over a period of 15 minutes at a temperature below 50°. The solution was allowed to stand an additional 15 minutes after which time a neutralized (10% acetic acid) aliquot gave a negative test with Fehling's solution. Ion-exchange resin [Dowex® 50W-X8 (H+)] was then added until the evolution of gas stopped and the mixture was stirred at room temperature for an additional hour. The mixture was then filtered, the resin washed with additional water and the filtrate concentrated at reduced pressure at a bath temperature of 35°, the last traces of water being removed by co-distillation with absolute ethanol to give an essentially quantitative yield of syrupy L-mannitol. A small portion (ca. 0.25 g.) was crystallized by dissolution in hot methanol and cooling to room temperature. The crystalline L-mannitol had the same chromatographic mobility (n-butanol/pyridine/water 10:3:3 v/v) as D-mannitol and had m.p. 164.5°–165° and $[\alpha]_D-0.9°$ (c 2.2, water). These physical constants are in good agreement with those found for D-mannitol.

EXAMPLE 9

1,3:2,5:4,6-Tri-O-methylene-L-mannitol (47)

To 50 g. of L-mannitol in a 500 ml. round-bottomed flask was added formaldehyde solution (36%, 100 ml.) and concentrated hydrochloric acid (100 ml.). The flask was fitted with a calcium chloride drying tube and the solution was heated on a water bath (90°) for three hours with frequent stirring, followed by heating at 75° for twenty hours. The fine crystals which had precipitated were cooled in an ice bath and removed by filtration, using a sintered glass funnel, and washed with a minimum of cold water. The filtrate could be treated with additional formaldehyde solution and hydrochloric acid to obtain an increased yield and this step was normally carried out. The crystalline mass was air dried, and subsequently dried in a desiccator over potassium hydroxide under reduced pressure to give pure tri-O-methylene-L-mannitol (55 g., 92%) having m.p. 226°–227°, and $[\alpha]_D+105°$ (c 2.0, chloroform). This compares well with tri-O-methylene-D-mannitol which has been found to have m.p. 232°–233° (corr.) and $[\alpha]_D-104.2°$ (c 2.19, chloroform).

EXAMPLE 10

1,6-Di-O-acetyl-3,4-di-O-(acetoxymethyl)-2,5-O-methylene-L-mannitol (48)

An acetolysis reaction carried out to obtain the title compound was performed by adding rapidly, with stirring, tri-O-methylene-L-mannitol (32 g., powdered, dry) to 160 ml. of an ice-cold acetolysis mixture (prepared by adding concentrated sulfuric acid (2 ml.) dropwise to an ice-cold mixture of acetic anhydride (140 ml.) and glacial acetic acid (60 ml.)). Within 15–20 minutes the reaction mixture set to a mass fine needle-like crystals. The mass was broken up and poured into three liters of ice-water and left at 5° for approximately eighteen hours. The precipitate was then removed by filtration and air dried. A chloroform extraction of the mother liquor yielded a small additional amount of product. The product was recrystallized from ethanol to give pure material (54 g., 90%) having m.p. 123°–124°, $[\alpha]_D-58°$ (c 1.0, chloroform). The D-isomer which was originally prepared by Ness, Hann and Hudson [J. Amer. Chem. Soc., 65, 2215 (1943)] has m.p. 129°–130°, and $[\alpha]_D+57.6°$ (c 1.1, chloroform).

EXAMPLE 11

2,5-O-Methylene-L-mannitol (49)

To a stirred solution of 1,6-di-O-acetyl-3,4-di-O-(acetoxymethyl)-2,5-O-methylene-L-mannitol (19 g.) in dry chloroform (200 ml.), cooled to 0° in an ice bath, was added 0.2 N methanolic sodium methoxide (19 ml.). Within an hour the solution deposited a crystalline precipitate. The mixture was then placed in a refrigerator at 5° and stirred for four days prior to removal of the product by filtration. The mother liquor was treated with an additional portion of sodium methoxide solution (10 ml.) to obtain additional product after two more days in the cold. The combined products were recrystallized from 95% ethanol as white prismatic needles which were obtained by filtration and air dried. The mother liquors were concentrated at reduced pressure and subsequently cooled to give a second crop of crystals. The pure 2,5-O-methylene-L-mannitol (8.6 g. 95%) had m.p. 174.5°–175.5°, and $[\alpha]_D+51.3°$ (c 3.1, water) compared to m.p. 173°–174° (corr.), and $[\alpha]_D-51.4°$ (c 1.2, water) reported for the D-isomer.

EXAMPLE 12

1,3,4,6-Tetra-O-benzyl-2,5-O-methylene-L-mannitol (50)

A vigorously stirred mixture of 2,5-O-methylene-L-mannitol (8.0 g.), benzyl chloride (80.0 ml.), and powdered potassium hydroxide (40.0 g.) was slowly heated to 115°–125° and kept in this temperature range for six hours. The mixture was then cooled, water (200 ml.) added, and the mixture was steam distilled for 5 hours. The solution was then cooled, the organic layer (lower) separated in a separatory funnel and the aqueous layer extracted with three 100 ml. portions of ether which were then added to the organic layer. The combined organic layer was then extracted with three 100 ml. portions of water, dried over magnesium sulfate, and evaporated under reduced pressure to a syrup. The syrup was dissolved in methanol (35 ml.) and the solution cooled in an ice bath. Water was added until turbidity persisted and the solution was left to stand at 5° overnight. The crystalline product was removed by filtration, dissolved in isopropyl ether to which was added some methanol, and the resultant solution cooled at 5° while crystallization progressed. The filtered crystals were washed with a solution of pentane-isopropyl ether (1:2, v/v) and air dried to give pure 1,3,4,6-tetra-O-benzyl-2,5-O-methylene-L-mannitol (16.2 g. 71%) having m.p. 53°–54°, and $[\alpha]_D + 6.4°$ (c 1.09, chloroform) as compared with m.p. 55°–56°, and $[\alpha]_D - 6.6°$ (c 1.02, chloroform) which were found for the D-isomer.

EXAMPLE 13

1,3,4,6-Tetra-O-benzyl-L-mannitol (51)

1,3,4,6-Tetra-O-benzyl-2,5-O-methylene-L-mannitol (7.5 g.) and phloroglucinol (14.3 g.) were dissolved in 1,4-dioxane (400 ml.) and the solution was diluted with 0.6 M hydrochloric acid (290 ml.). The reaction mixture was boiled gently under reflux for 24 hours, at which time t.l.c. (Solvent C) showed the hydrolysis to be complete. To this solution was then added concentrated hydrochloric acid (30 ml.) and heating was continued for a further 12 hours. The mixture was then cooled and concentrated under reduced pressure to a dry crystalline mass which was shaken with dichloromethane (75 ml.) at room temperature. Unchanged phloroglucinol was removed by filtration and washed with more dichloromethane (40 ml.). The combined filtrate and washings were washed with aqueous sodium hydrogen carbonate (saturated solution) and then with water. The solution was dried over magnesium sulfate, filtered through a pad of Celite and decolorizing charcoal and then concentrated to a syrup which was dissolved in a 5:6 mixture of ether and pentane. Crystallization was allowed to progress at 5° to give 5.5 g. (75%) of product in two crops. The product was recrystallized from isopropyl ether to give pure 1,3,4,6-tetra-O-benzyl-L-mannitol, m.p. 52.5°–53°, $[\alpha]_D - 31.5°$ (c 2.6, chloroform). These values compared favourably with the data obtained for the D-isomer m.p. 55°–56°, and $[\alpha]_D + 31.2°$ (c 0.87, chloroform).

EXAMPLE 14

1,3,4,6-Tetra-O-benzyl-L-fructofuranose (45)

To a magnetically stirred solution of 1,3,4,6-tetra-O-benzyl-L-mannitol (1.0 g.) in acetone (100 ml.) was added, dropwise, a solution of Jones' Reagent [8.7 ml. of sulfuric acid added dropwise to a cooled (0°) solution of 10.3 g. of chromium trioxide in 30 ml. of water]. After the addition of 1.65 ml. of the reagent, there appeared a persistent red coloration of the reaction mixture, in marked contrast to the previous green color which was due to the chromic salts. T.L.C. (Solvent D) of the reaction mixture showed that no starting material remained, and that in fact two new components were present, the major component having $R_f \approx 0.4$, and the minor one having $R_f \approx 0.74$, as opposed to an observed $R_f$ value of approximately 0.21 for the starting material. An additional 0.05 ml. of the reagent was added and the solution was stirred for a further 15 minutes. The solution was then diluted with water (100 ml.) and the resultant mixture extracted with ether (3 × 75 ml.). The ether layer was neutralized with aqueous sodium hydrogen carbonate, washed with water, dried over magnesium sulfate, and concentrated under reduced pressure to a syrup (1.0 g.). The syrup was chromatographed on a column of silica gel (50 g.) to obtain 0.122 g. of the faster, minor component and 0.714 g. of the major component.

The syrupy minor component had an infrared spectrum which showed a strong carbonyl absorption and no absorption characteristic of a hydroxyl group. The p.m.r. spectrum was consistent in that no hydroxyl proton signal could be observed and a total of 34 protons were observed. Upon dissolution of this syrup in isopropyl ether and leaving the solution at 5° for a prolonged period of time (allowing the solvent to slowly evaporate), crystallization of this product occurred. This crystalline product had an i.r. spectrum indistinguishable from that of the syrup and had m.p. 68°–69°, and $[\alpha]_D - 16.2°$ (c 5.0, chloroform). This compound is considered to be the diketose formed by the oxidation of both of the free hydroxyl groups of 1,3,4,6-tetra-O-benzyl-L-mannitol.

The major component (syrup) was chromatographically indistinguishable (t.l.c., benzene/diethyl ether 6:1 v/v) from previously prepared, crystalline 1,3,4,6-tetra-O-benzyl-D-fructofuranose [m.p. 42°–43°, $[\alpha]_D + 6.0° \rightarrow +11.4°$ (24 hr., c 1.5, chloroform) as compared with m.p. 42°–43°, $[\alpha]_D + 6.5° \rightarrow +8.7°$ (25 hr., c 1.43, chloroform) which has been reported previously for this D-isomer]. The p.m.r. spectrum showed absorptions at $\tau 2.7$ (20 aromatic protons), $\tau 5.4$–$6.5$ (16 protons, ring protons, benzylic —CH$_2$—), and one exchangeable (D$_2$O) hydroxyl proton at $\tau 6.0$). This spectrum was identical to that obtained for the crystalline D-isomer. Furthermore, this syrupy compound had $[\alpha]_D - 12.6°$ (c 3.7, chloroform) as compared with an equilibrium value of $[\alpha]_D + 11.4°$, and $[\alpha]_D + 8.7°$, which had been previously obtained for the D-isomer.

Catalytic hydrogenation of a sample of this compound in methanol at 30 psig for 2 hours over a 5% palladium-on-charcoal catalyst produced a syrup which was homogeneous on paper (n-butanol/pyridine/water 10:3:3 v/v) and which had a mobility equal to that of D-fructose.

EXAMPLE 15

1,3,4,6-Tetra-O-benzyl-β-L-fructofuranosyl 2,3,4,6-Tetra-O-benzyl-α-L-glucopyranoside (Octa-O-benzyl-L-sucrose)

A suspension of molecular sieves (type 3A, 2.5 g.) and silver carbonate (0.5 g.) in a solution of 1,3,4,6-tetra-O-benzyl-L-fructofuranose (0.5 g.) in dry benzene (3 ml.) was stirred under nitrogen, in the dark, at room temperature, for 10 minutes. Silver perchlorate (50 mg.) which had been dried by evaporating dry benzene from the salt was added to the mixture, stirring being continued. A solution of 2,3,4,6-tetra-O-benzyl-L-glucopyranosyl chloride, prepared as previously described from 0.5 g. of 2,3,4,6-tetra-O-benzyl-α-L-glucopyranose, in dry benzene (10 ml.), was then added dropwise over a period of 10 minutes. Within 10 minutes of the final addition, t.l.c. (benzene/diethyl ether 6:1) revealed the presence of two new components having mobilities of 0.84 and 0.8 compared to the mobility of the glycosyl halide, whereas the fructose derivative had a mobility of 0.46 and 2,3,4,6-tetra-O-benzyl-α-L-glucopyranose had a mobility of 0.26. The reaction was monitored continuously by t.l.c. and after 42 hours, as no glycosyl chloride could be detected, the reaction mixture was filtered through a pad of Celite ® and decolorizing charcoal. The residue was washed several times with dry benzene, and the combined filtrate concentrated at reduced pressure to a syrup (0.954 g.). The syrup was placed on a column of silica gel [200 g., prepacked in dichloromethane and treated with benzene (50 ml.) prior to use] and eluted with a 6:1 mixture of benzene and ether. The fractions containing the two faster components were combined and evaporated under reduced pressure to a syrup (0.342 g.) which was placed on a second column (150 g.) and eluted with a 25:1 mixture of benzene and ether in an attempt to separate the two components. This separation procedure yielded two chromatographically homogeneous components, the faster moving compound (72 mg.) having a mobility (t.l.c., benzene/diethyl ether 6:1 v/v) equal to that of previously prepared octa-O-benzyl-D-sucrose.

This faster component (octa-O-benzyl-L-sucrose) had an infrared spectrum identical to that of octa-O-benzyl-D-sucrose. The p.m.r. spectrum was also identical to that of the D-isomer, τ2.6–2.8 (40 aromatic protons), τ4.3 (1-proton doublet, $J_{1,2} \approx 4$ Hz, anomeric proton of the glucopyranosyl moiety), τ5.2–6.8 (29 protons, ring protons and benzylic —$CH_2$—). In order to ascertain that the correct α,β-linkage had been obtained a $^{13}$C-n.m.r. spectrum of this sample was obtained and this spectrum was compared with that of octa-O-benzyl-D-sucrose. In the latter spectrum absorptions at $\delta_{TMS}$ 104.6 and $\delta_{TMS}$ 89.8 had been respectively assigned to the anomeric carbon of the fructofuranosyl moiety and the anomeric carbon of the glucopyranosyl moiety, whereas the remainder of the carbon absorptions were left unassigned. The spectrum of octa-O-benzyl-L-sucrose showed the same "fingerprint" of absorptions in the range $\delta_{TMS}$ 68–84 (ring carbons except for the anomeric carbons, and the methylene carbons of the benzyl ether groups), and $\delta_{TMS}$ 127–139 (aromatic carbons). More importantly, however, was the appearance of anomeric-carbon signals at $\delta_{TMS}$ 90.0 (C-1 of the glucopyranosyl moiety) and $\delta_{TMS}$ 104.6 (C-2 of the fructofuranosyl moiety). These absorptions confirmed that the compound which had been isolated in fact had a β-fructofuranosyl α-glucopyranoside linkage.

Furthermore, this compound, when dissolved in chloroform showed a specific rotation of $[\alpha]_D - 35.6°$ (c 4.05, chloroform), whereas values of +38.6° and +31.6° have been recorded for the D-isomer in this solvent. Catalytic hydrogenation (5% palladium-on-charcoal), 35 psig, 3 hr. in methanol produced a compound which had a mobility on paper (n-butanol/pyridine/water 10:3:3 v/v) equal to that of D-sucrose. Filtration of the hydrogenation mixture followed by concentration of the filtrate under reduced pressure afforded a syrup which was dissolved in a small amount of water and the resultant solution was placed in an evacuated disiccator containing potassium hydroxide. After several days, the container was found to contain a dry crystalline material which had a melting point of 186°–188°, and which was strongly laevorotatory. The accepted melting point of D-sucrose is 184°–185°.

The slower moving component (60 mg.) showed a specific rotation of $[\alpha]_D - 41.5°$ (c 3.44, chloroform). The p.m.r. spectrum showed a one-proton doublet at τ4.3 with $J_{1,2} \approx 3$ Hz, a signal which is characteristic of an α-glucopyranoside derivative. The absorptions in the region τ5.0–6.8 were similar to, but definitely distinct from, those obtained from either octa-O-benzyl-D- or L-sucrose. The $^{13}$C-n.m.r. spectrum was again very similar to the spectrum obtained for octa-O-benzyl-D- or -L-sucrose. However, the absorption that was due to the anomeric carbon of the fructofuranosyl moiety (C-2) was found to occur at $\delta_{TMS}$ 108.6. This downfield shift of 4 ppm has been associated with an α-fructofuranoside derivative. It was thus concluded that this second component was 1,3,4,6-tetra-O-benzyl-α-L-fructofuranosyl 2,3,4,6-tetra-O-benzyl-α-L-glucopyranoside.

From the original reaction mixture some 1,3,4,6-tetra-O-benzyl-L-fructofuranose (0.217 g.) was obtained along with some crystalline 2,3,4,6-tetra-O-benzyl-α-L-glucopryanose (0.173 g.). Therefore, based on the 1,3,4,6-tetra-O-benzyl-L-fructofuranose which had not reacted, a yield of 13% of octa-O-benzyl-L-sucrose was obtained along with a 10% yield of the α,α-linked octa-O-benzyl disaccharide.

EXAMPLE 16

About 100 mg. of L-sucrose was produced by the process as described in Example 15 and a small sample thereof was tasted by an investigator and found to be sweet.

EXAMPLE 17

Hamster jejunal brush border enzyme test for metabolism

A sample (11 mg.) of L-sucrose was dissolved in 0.60 ml. maleate buffer (pH 6.0) which was then divided into two 0.3 ml. aliquots. 70 mg. of purified brush border enzyme dissolved in 0.2 ml. of maleate buffer was added to one aliquot (test sample) and 0.2 ml. of maleate buffer only was added to the other aliquot (blank). Both the test sample and the blank were then incubated for 30 minutes in a shaker bath at 60 strokes per minute and at a temperature of 37° C. No attempt was made to stop the reaction. After further incubation for 24 hours at 37° C. with without shakings, the blank and test samples were spotted directly on precoated silica gel 60F—254 glass plates (Merck), impregnated with 0.5 M $NaH_2PO_4$ (Hansen, J. Chromatog. 107 (1975) 224). A mixture of glucose, fructose and sucrose was also spotted onto the plates, in order to provide reference standards. The chromatogram was developed in isopropanol:acetone: 0.1 M lactic acid 4:4:2 by volume. The components were detected by spraying the developed plate with aniline-diphenylamine-acetone-80% $H_3PO_4$ (4 ml. - 4 g. - 200 ml. - 30 ml.) and heating to 105° C. for 30 minutes. The glucose standard appeared as a blue spot, the fructose standard as a red spot and the sucrose standard as a violet spot. Both the blank and test sample showed a single violet spot corresponding in both position and colour to the sucrose standard spot on the same plate. The $R_F$ values were: sucrose 0.39, fructose 0.35, glucose 0.28, blank sample 0.39 and test sample 0.39. These results indicate that no detectable amounts of free glucose or fructose were present in the test sample as a result of the exposure of L-sucrose to the sucroses of the hamster jejunal brush border membrane. Similarly, there was no free glucose or fructose present in the blank sample as a result of an identical treatment but in the absence of the brush border membrane. It is concluded, therefore, that L-sucrose is not metabolized as defined by a standard metabolism test.

EXAMPLE 18

Flavour testing of L-sucrose (a) A series of 0.5 ml. test solutions were prepared by a single experimenter, in the presence of a witness, containing (a) 2.5% by weight L-sucrose and (b) 1.25% by weight D-sucrose, respectively in water. A series of 0.5 ml. blank solutions containing only distilled water were also prepared. The sample vials were each coded on the bottom thereof using a code known only to the experimenter and the witness, and 5 sample vials were placed in a circle on a tray with a glass of rinse water by the witness. Each prepared tray had one L-sucrose sample, one D-sucrose sample and three blank samples. A third person, not present during the preparation, carried a prepared tray into the test room, separate from and out of view of the preparation room and invited a test subject, who had been made to feel as comfortable as possible, to sample each vial in any order and state whether or not it was sweet and, if possible, how sweet it was in relation to the other samples. The test subject was permitted to drink the entire sample or any suitable portion thereof and was asked to rinse his mouth thoroughly with the rinse water provided between each sample and to be sure no after-taste remained from the previous sample before testing the next sample. The response record was signed and witnessed and finally the data of the solutions tested was matched to the response record.

| Test Subject A | | |
|---|---|---|
| Sample | Response | Sample Content |
| 1 | not sweet | water |
| 2 | sweet | 2.5% L-sucrose |
| 3 | not sweet | water |
| 4 | sweet | 1.25% D-sucrose |
| 5 | not sweet | water |
| Test Subject B | | |
| Sample | Response | Sample Content |
| 1 | not sweet | water |
| 2 | sweet | 1.25% D-sucrose |
| 3 | not sweet | water |
| 4 | sweet | 2.5% L-sucrose |
| 5 | not sweet | water |

(b) A second series of 0.1 ml. samples were prepared using the same procedures to ensure secrecy as in (a) above, and administered to different test subjects using a disposable pipette for each solution. Three to four drops were applied to the front of the tongue and the test subject rolled the sample over the tongue. The response of "sweet" or "not sweet" was recorded as before. The subject was also allowed to repeat the tasting of any sample to confirm or change his response, and was asked to rinse thoroughly with rinse water between samples and to be sure that no after-taste remained from the previous sample before testing the next sample.

| Test Subject C | | | |
|---|---|---|---|
| Sample | Comparison | Sample Content | |
| 1 | sweet | sweeter than 5 | 3.75% D-sucrose |
| 2 | sweet | sweeter than 5 sweet as 1 | 10% L-sucrose |
| 3 | not sweet | | water |
| 4 | sweet | least sweet | 10% L-sucrose |
| 5 | sweet | sweeter than 4 | 5% D-sucrose |
| Test Subject D | | | |
| Sample | Response | Sample Content | |
| 1 | sweet | 10% L-sucrose | |

Although difficult to establish relative sweetness by an empirical taste test of this nature, the results hereinabove clearly indicate that L-sucrose appeared sweet to the taste of all test subjects.

We claim:

1. β-L-fructofuranosyl α-L-glucopyranoside.

* * * * *